US006258970B1

(12) United States Patent
Ward, III et al.

(10) Patent No.: US 6,258,970 B1
(45) Date of Patent: Jul. 10, 2001

(54) METHOD FOR PROMOTING DIALKYLDIHALOSILANE FORMATION DURING DIRECT METHOD ALKYLHALOSILANE PRODUCTION

(75) Inventors: William Jessup Ward, III, Niskayuna; Larry Neil Lewis, Scotia; John Matthew Bablin, Amsterdam; David Cheney DeMoulpied, Clifton Park, all of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/571,836

(22) Filed: May 16, 2000

Related U.S. Application Data

(63) Continuation-in-part of application No. 09/293,798, filed on Apr. 19, 1999, now abandoned.

(51) Int. Cl.[7] ....................................................... C07F 7/16
(52) U.S. Cl. ............................................................ 556/472
(58) Field of Search ................................................ 556/472

(56) References Cited

U.S. PATENT DOCUMENTS

| 2,380,995 | 8/1945 | Rochow . |
| 4,500,724 | 2/1985 | Ward et al. . |
| 4,602,101 | 7/1986 | Halm et al. . |
| 4,762,940 | 8/1988 | Halm et al. . |
| 4,898,960 | 2/1990 | Dosaj et al. . |
| 4,946,978 | 8/1990 | Halm et al. . |
| 5,059,343 | 10/1991 | Halm et al. . |
| 5,059,706 | 10/1991 | Degen et al. . |
| 5,281,739 | 1/1994 | Halm et al. . |
| 5,596,119 | 1/1997 | Halm et al. . |
| 5,847,181 | 12/1998 | Nakanishi et al. . |
| 5,874,604 | * 2/1999 | Steiner et al. ................ 556/472 |
| 6,005,130 | 12/1999 | Lewis et al. . |

FOREIGN PATENT DOCUMENTS 9501303   1/1995   (WO) .

OTHER PUBLICATIONS

"Polymeric Methyl Silicon Oxides" by E. G. Rochow and W.F. Gilliam, Journal of the American Chemical Society, 63 798 (1941).
International Search Report.

* cited by examiner

Primary Examiner—Paul F. Shaver
(74) Attorney, Agent, or Firm—Bernadette M. Bennett; Noreen C. Johnson

(57) ABSTRACT

A method is described for enhancing the formation of alkylhalosilane during the direct method reaction between powdered silicon and a catalyst comprising copper, zinc, tin, and phosphorus. An increase in the value of the Cu/Zn weight ratio has been found to promote the performance of the phosphorus-containing catalyst as shown by in an increase in the weight percent dimethyldichlorosilane in methylchlorosilane crude.

18 Claims, 1 Drawing Sheet

METHOD FOR PROMOTING DIALKYLDIHALOSILANE FORMATION DURING DIRECT METHOD ALKYLHALOSILANE PRODUCTION

This application is a continuation-in-part of application Ser. No. 09/293,798, filed Apr. 19, 1999, now abandoned.

BACKGROUND OF THE INVENTION

The present invention is directed to a method for enhancing the formation and recovery of dialkyldihalosilane from alkylhalosilane crude. More particularly, the present invention relates to a direct method for methylchlorosilane manufacture by maintaining a low weight ratio of zinc with respect to copper while using phosphorus as a catalyst for enhancing dimethyldichlorosilane formation.

The Rochow Direct Method Process for making methylchlorosilanes by effecting reaction between powdered silicon and methyl chloride in the presence of a copper catalyst is shown by U.S. Pat. No. 2,380,995. As taught by Rochow in Chemistry of the Silicones, Second Edition, (1951), John Wiley and Sons, New York, pp. 79–80, dimethyldichlorosilane is the source of dimethylsiloxy, or "Di" units when hydrolyzed, and is basic for the manufacture of high molecular weight polymers. It has been long recognized, as shown by Rochow et al., *J. Am. Chem. Soc.*, 63, 798 (1941) that in addition to copper, key metallic promoters, such as zinc and tin, also can enhance the formation of dimethyldichlorosilane during direct method methylchlorosilane crude production.

T. Margaria et al., WO/95/01303, (1994) have further described the use of phosphorus as a promoter for dimethyldichlorosilane formation in the direct method. Copper phosphide has been cited by Halm et al., in U.S. Pat. No. 4,762,940 (1990), as a useful source of phosphorus for improving dimethyldichlorosilane selectivity in direct method procedures. As shown in U.S. Pat. No. 5,059,343, Halm et al., also investigated the effects of using phosphorus to improve dimethyldichlorosilane selectivity in direct method operations in combination with copper, tin and zinc. Even though significant advances have been made with respect to procedures for improving the yields of dimethyldichlorosilane in direct method methylchlorosilane manufacture, further techniques are constantly being sought.

SUMMARY OF THE INVENTION

A method is provided for promoting the formation of dialkyldihalosilane during direct method alkylhalosilane production. The method comprises effecting reaction between alkylhalide and powdered silicon in the presence of a catalyst comprising copper (Cu), silicon (Si), zinc (Zn), and phosphorus (P), where there is maintained during alkylhalosilane formation a reaction mixture comprising, by weight, an average proportion of copper in a range between about 1% and about 5% based on the weight of silicon;

a sufficient amount of zinc to provide a Cu/Zn weight ratio having a value in a range between about 25 and about 250;

and a proportion of phosphorus in a range between about 100 ppm and about 1000 ppm, based on the weight of reaction mixture.

DETAILED DESCRIPTION OF THE INVENTION

Figure 1:
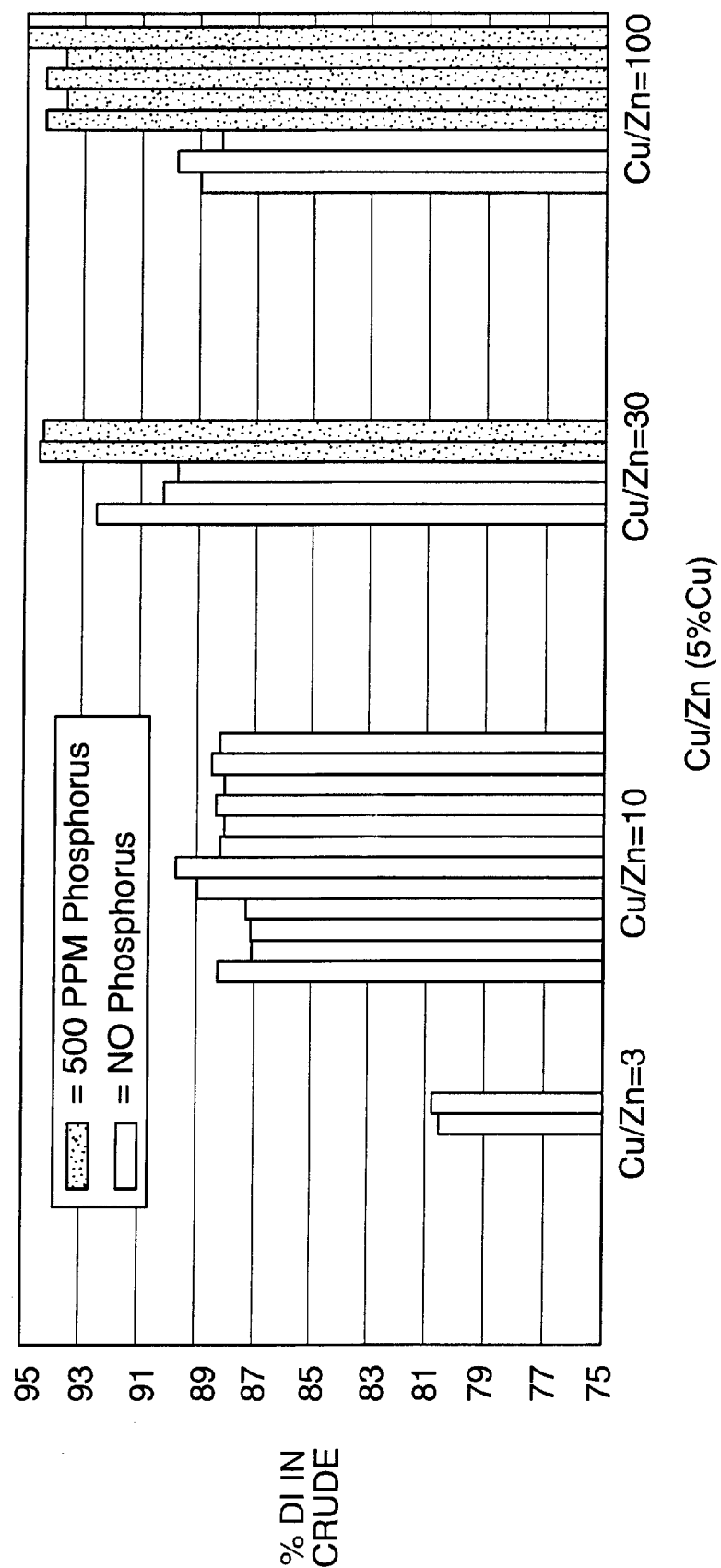
FIG. 1 shows gas chromatography results of dimethyldichlorosilane produced at varying Cu/Zn weight ratios with and without phosphorus.

The present invention provides for enhanced effectiveness of the methylchlorosilane reaction. While phosphorus is recognized as a dimethyldichlorosilane catalyst, its effectiveness for dimethyldichlorosilane formation during direct method operation can be substantially enhanced by introducing phosphorus into the reactor while maintaining a high weight ratio of copper to zinc in a range between about 25 and about 250. Preferably, the weight ratio of copper to zinc is in a range between about 30 and about 200 and more preferably, in a range between about 35 and about 100. "Substantially enhanced" dimethyldichlorosilane formation as used herein refers to an increase in the percentage of dimethyldichlorosilane produced by at least about 3%. The level of phosphorus and the copper to zinc ratio have a synergistic effect on the process for making dimethyldichlorosilane. Phosphorus is present in a range between about 100 ppm and about 1000 ppm based on the weight of reaction mixture. If the zinc level is too low or too high, the addition of phosphorus does not have an effect on the amount of the dimethyldichlorosilane produced.

Although methyl chloride is the alkyl halide of choice for the alkylhalosilane reaction, other alkyl halides such as $C_{1-4}$ alkyl chlorides, for example, ethyl chloride, propyl chloride, etc., also can be used. Correspondingly, the term "alkylhalosilane" includes dialkylhalosilanes such as dimethyldichlorosilane (Di), which is the preferred methylchlorosilane, and a variety of other alkylhalosilanes such as trimethylchlorosilane (Mono), methyltrichlorosilane (Tri), silicon tetrachloride, trichlorosilane, methyldichlorosilane (MH), and dimethylehlorosilane ($M_2H$), and also tetramethylsilane.

Among the processes which can be used in the practice of the invention, there are included those in which at least one reactor comprises a fixed bed, a stirred bed, or a fluid bed. The invention can be practiced in a continuous, semi-continuous, or batch manner. More specifically, a fixed bed reactor may be a column that contains silicon particles through which alkyl halide gas passes. A stirred bed may be similar to a fixed bed in which there is mechanical agitation of some sort in order to keep the bed in constant motion. Reaction typically occurs at a temperature in a range between about 250° C. and about 350° C., and preferably in a range between about 280° C. and about 320° C. It is also advisable to carry out the reaction under a pressure in a range between about 1 atmosphere and about 10 atmospheres in instances where a fluid bed reactor is used since higher pressure increases the rate of conversion of methyl chloride to methylchlorosilanes. Desirably, the pressure is in a range between about 1.1 atmospheres and about 3.5 atmospheres and preferably in a range between about 1.3 atmospheres and about 2.5 atmospheres.

The expression "semi-continuous conditions" with respect to the description of processes means that reactants are added and the reactor is run until about 50% of the silicon has been utilized. After about 50% silicon utilization, additional reactants of silicon and catalysts may be added. With a batch mode reaction, all of the reactant components are combined and reacted until most of the reactants are consumed. In order to proceed, the reaction has to be stopped and additional reactants added. A fixed bed and stirred bed may both be run under batch conditions. A fluidized reactor is typically run under continuous conditions. With continuous conditions, the reaction does not have to be stopped in order to add more reactants In instances where a fluid bed reactor is used, methyl chloride, an inert gas such as argon, or mixture thereof can be used to fluidize the bed of silicon particles. The silicon particles can have an average size below about 700 microns, with an average size of greater than about 20 microns and less than about 300 microns being preferred. Preferably, the mean diameter of the silicon particles is in a range between about 100 microns and about 150 microns. Silicon used in the alkylhalosilane reaction can have an iron (Fe) content in a range between about 0.1% and about 1% by weight based on total silicon, calcium (Ca) content in a range between about 0.01% and about 0.2% by weight based on total silicon, and an aluminum (Al) content in a range between about 0.02% and about 0.5% by weight based on total silicon. Silicon is usually obtained at a purity of at least about 98% by weight of silicon and it is then comminuted to particles of silicon in the above-described range for preparation of the contact mass. "Contact mass" as used herein refers to a source of copper which is pre-reacted with a silicon powder to form a contact mass. The contact mass is typically prepared by reacting silicon and cuprous chloride at a temperature in a range between about 280° C. and about 400° C. in a furnace until evolution of silicone tetrachloride ($SiCl_4$) ceases. The resulting solid contains silicon and copper and is called contact mass. The contact mass is added to the reactor with other catalyst components.

The sources of phosphorus that may be used include, but are not limited to, copper phosphide ($Cu_3P$), zinc phosphide ($Zn_3P_2$), phosphorous trichloride ($PCl_3$), alkylphosphines ($R_3P$) such as triethylphosphine $[(C_2H_5)_3P]$ and trimethylphosphine $[(CH_3)_3P]$, and combinations thereof.

Among the copper compounds which can be used as copper sources in the practice of the invention are carboxylate salts of copper, and partially oxidized copper. Additional copper sources include, but are not limited to, particulated cupric chloride and cuprous chloride, copper flake, brass, bronze, and combinations thereof.

Examples of effective sources of zinc include, but are not limited to, zinc metal powder; halides of zinc, such as zinc chloride; zinc oxide; and combinations thereof. Relative to copper and tin weight ratios, tin can be present in the reaction mixture during dialkyldihalosilane formation, in a range between about 200 ppm and about 3000 ppm of tin per part of the total weight of the reaction mixture. Sources of tin include, but are not limited to, tin metal dust, tin halides, tin oxide, tetramethyl tin, alkyl tin halides, brass, bronze, and combinations thereof.

Analysis is conducted to determine crude composition. Silicon utilization is determined by weighing crude samples at various times. Typically data is recorded at about 20% by weight silicon utilization. Selectivity is determined by gas chromatography, "GC", with thermal conductivity detectors. Individual silane component analysis is performed by analysis of reagent grade. GC calibrations are performed by analysis of silane mixtures of known composition.

The graph in FIG. 1 shows the impact phosphorus can have, at a 500 ppm level, on promoting dimethydichlorosilane formation during direct method methylchlorosilane production. The data are based on operating a fixed bed at about 20% silicon utilization, over a broad Cu/Zn weight ratio range, employing copper phosphide as a phosphorus source. As shown by the graph, Cu/Zn ratio values at about 30:1 and about 100:1 are particularly effective for increasing the efficiency of the process of making dimethyldichlorosilanes.

In order that those skilled in the art will be better able to practice the present invention, the following examples are given by way of illustration, and not by way of limitation. All parts are by weight unless otherwise indicated.

EXAMPLE 1

A fixed bed reactor, as shown by FIG. 1, was used in a dimethyldichlorosilane process study. The fixed bed reactor was a glass tube 20 centimeters (cm) long having a 1.3 cm outside diameter. A glass frit was located 6 cm from the end to support a bed of powdered silicon. The bed size was 6 grams (g). The highest anticipated reaction rate was about 1 gram crude/hour-gram silicon.

Silicon powder used in the study was furnished by Elkem Co. of Alloy, W. Va. The silicon powder was ground to achieve an average surface area of 0.38 meters$^2$/gram. The major elemental components expressed in parts per million present in the silicon were aluminum (1800), calcium (20), iron (5000), and phosphorus (40). Several of the catalyst sources, such as cuprous chloride, powdered tin, and powdered zinc used in the study were obtained from the Aldrich Co. of Milwaukee, Wis.

The contact mass was prepared as follows:

A mixture of 40 grams (g) of silicon powder (0.38 micron particle size), and 5.43 g of hexane were combined with a hexane slurry of 12.67 g of solids consisting of CuCl and tin dust having a Cu/Sn ratio of 1000:1. The mixture was initially dried with a stream of nitrogen under ambient conditions, and then fully dried under reduced pressure at ambient temperatures.

The pre-contact mass was placed in a crucible and then into a furnace and heated to 300° C. under a flow of argon until silicon tetrachloride ($SiCl_4$) evolution ceased. An ammonium hydroxide ($NH_4OH$) indicator was used to monitor the effluent. The weight change due to loss of volatile products accompanying the reaction to prepare contact mass was within experimental error equal to the calculated weight loss.

The fixed bed reaction was run over a period of 8 hours at a temperature in a range between about 300° C. and about 310° C. There was used a contact mass based on an initial charge of 6 g of powdered silicon, and 5% by weight copper of the contact mass in the form of copper chloride (CuCl). Sufficient powdered tin and powdered zinc were also blended into the contact mass to provide tin (Sn) having a value of about 1000 ppm, and a Cu/Zn ratio having a value of 10:1. A methyl chloride flow rate was maintained at 35 milliliters/minute. After about 20% silicon utilization, based on weight of crude formed, the selectivity for dimethyldichlorosilane was found by gas chromatography to be 86.6%.

Following substantially the same procedure, a series of fixed bed reaction runs were made involving the use of contact mass carried to at least about 20% silicon utilization, with and without phosphorus at initial Cu/Zn ratios at 10:1 and 100:1.

Prior to charging the reactor, appropriate levels of zinc dust, and sources of phosphorus, such as copper phosphide ($Cu_3P$) were blended into the contact mass. Volatile phosphorus compounds, such as trichlorophosphine ($PCl_3$), and trimethylphosphine $[(CH_3)_3P]$, were injected upstream with methyl chloride flow into the contact mass at a rate in a range between about 0.15 milligrams of phosphorus per minute and about 0.20 milligrams of phosphorus per minute.

The following Table shows the results obtained, where "Di" is dimethyldichlorosilane:

TABLE 1

| Cu Source | Cu/Zn Ratio | P(ppm as $(CH_3)_3P$) | % Di at 20% Si Utilization |
|---|---|---|---|
| CuCl | 10:1 | 0 | 89.7 |
| CuCl | 10:1 | 500 | 88.4 |
| CuCl | 100:1 | 0 | 85.6 |
| CuCl | 100:1 | 500 | 94.2 |

Consistent with the results of FIG. 3, a significant dimethyldichlorosilane promotional effect was shown as a result of the use of 500 ppm of phosphorus at Cu/Zn ratios of 100:1. For example, at 0 ppm phosphorus a 85.6% dimethyldichlorosilane level was obtained, while at 500 ppm of phosphorus, a 94.2% dimethyldichlorosilane level was obtained. However, when the ratio of copper to zinc was 10:1, the percent dimethyldichlorosilane produced was not substantially enhanced with or without the added phosphorus.

EXAMPLE 2

The fixed bed reaction procedure of example 1 was substantially repeated, except the phosphorus source was triethylphosphine, $(C_2H_5)_3P$. A silicon blend containing 4.75% by weight copper as copper chloride and 50 ppm of tin dust were used. The blend (6.17 g) along with 1.0 milligrams (mg) of zinc dust (Cu/Zn ratio of 300:1) was added to the glass fixed bed reactor. At a bed temperature in a range between about 220° C. and about 250° C. methyl chloride was passed through the bed. Five equal aliquots of $(C_2H_5)_3P$, the sum total of 3.0 mg phosphorus or 500 ppm relative to silicon, were injected upstream of the bed at a rate in a range between about 0.15 milligrams of phosphorus per minute and about 0.20 milligrams of phosphorus per minute. The reaction was run with a methyl chloride flow rate of 35 milliliters per minute. The reaction was run in triplicate. Average results can be seen in Table 2.

EXAMPLE 3

The experiment in example 2 was repeated except that during heat up of the bed with methyl chloride flowing, no phosphorus was injected upstream of the bed. Results can be seen in Table 2.

EXAMPLE 4

The silicon blend of example 2 (6.17 g) along with 1.4 mg of zinc dust (Cu/Zn ratio of 200:1) was added to the glass fixed bed reactor. At a bed temperature in a range between about 220° C. and about 250° C. methyl chloride was passed through the bed. Five equal aliquots of $PR^1_3$ ($R^1$ being methyl or ethyl; the sum total of 3.0 mg phosphorus, or 500 ppm relative to silicon) were injected upstream of the bed at a rate in a range between about 0.15 milligrams of phosphorus per minute and about 0.20 milligrams of phosphorus per minute. The reaction was run with a methyl chloride flow rate of 35 mL/min. The reaction was run in triplicate. Average results can be seen in Table 2

EXAMPLE 5

The experiment in example 4 was repeated except that during heat up of the bed with methyl chloride flowing, no phosphorus was injected upstream of the bed. The reaction was run in triplicate. Average results can be seen in Table 2.

TABLE 2

| Cu/Zn Ratio | P(ppm) | % Di | % Tri | % Mono | % MH | Residue |
|---|---|---|---|---|---|---|
| 300:1 | 500 | 89.80 | 3.89 | 2.39 | 0.72 | 2.95 |
| 300:1 | 0 | 87.23 | 4.54 | 3.13 | 0.89 | 3.84 |
| 200:1 | 500 | 92.79 | 2.34 | 1.72 | 0.58 | 2.37 |
| 200:1 | 0 | 87.09 | 4.18 | 2.84 | 0.67 | 4.93 |

The results from examples 2–5 of percent dimethyldichlorosilane at about 20% silicon utilization indicate that there was no significant improvement in the percent dimethyldichlorosilane produced by adding phosphorus to the 300:1 Cu/Zn bed. When comparing the percent dimethyldichlorosilane at 89.80 (standard deviation 0.75) when Cu/Zn=300:1 with 500 ppm phosphorus and the percent dimethyldichlorosilane at 87.23 (standard deviation 1.36) when Cu/Zn=300:1 with 0 ppm phosphorus, the addition of phosphorus does not substantially enhance the efficiency of the dimethyldichlorosilane produced. In contrast, when the copper to zinc ratio was 200:1, the addition of phosphorus resulted in 92.79% Di (standard deviation 0.54) compared to no phosphorus, 87.09% Di (standard deviation 0.05). The addition of phosphorus substantially enhanced the percent dimethyldichlorosilane produced.

EXAMPLE 6

The fixed bed reaction procedure of example 1 was substantially repeated, except in place of contact mass, the source of copper is copper flake and powdered brass obtained from OMG Americas, Research Triangle Park, N.C. The brass comprised by weight, 80% copper, 19.5% zinc and 0.5% tin.

The fixed bed reactions were conducted at 5% by weight copper levels, based on bed weight, comprising blends of powdered silicon, copper flake and appropriate amounts of brass. Master batch slurries in hexane or toluene of silicon, copper flake, and brass were made. A Cu/Zn weight ratio of about 11:1 was made using 135 g of silicon, 4.29 g of copper flake, and 3 g of brass. Another slurry was prepared to provide a Cu/Zn weight ratio of 35:1. The solvent was separated under reduced pressure, prior to charging the resulting blend into the fixed bed reactor.

The following results were obtained, employing trimethylphosphine at 0 ppm and 500 ppm, and at Cu/Zn weight ratios of 11:1 and 35:1.

TABLE 3

| Cu Source | Cu/Zn Ratio | P(ppm as $(CH_3)_3P$) | % D at 20% Si Utilization |
|---|---|---|---|
| Cu flake | 11:1 | 0 | 88.3 |
| Cu flake | 11:1 | 500 | 90.8 |
| Cu flake | 35:1 | 0 | 83.3 |
| Cu flake | 35:1 | 500 | 91 |

EXAMPLE 7

A fluid bed reactor was used in a direct method study. There was employed a copper/zinc catalyst to determine whether the effectiveness of phosphorus as a dimethyldichlorosilane promoter was influenced by the particular Cu/Zn weight ratio range used during the reaction. The fluid bed reactor consisted of a 3.8 cm interior diameter (ID) glass tube with a glass frit at the center to support the silicon bed.

The reactor was enclosed in a glass heating tube which was wrapped in Nichrome wire. In order to fluidize the bed, a stirrer was used in combination with a vibrator.

The reactor was initially charged with 20 g of contact mass having 5% copper and a starting Cu/Zn weight ratio of 10:1. Methyl chloride was fed into the reactor over a period in a range between about 24 hours and about 28 hours at a bed temperature in a range between about 300° C. and about 310° C. After 35% silicon utilization, the crude was analyzed for percent dimethyldichlorosilane by gas chromatography. The same procedure was repeated, except that the bed included 10 mg of $Cu_3P$, which provided 500 ppm of phosphorus.

A similar fluid bed procedure was repeated with and without 10 mg of copper phosphide, except a Cu/Zn weight ratio of 100:1 was used. The Cu/Zn weight ratios of 10:1 and 100:1 were respectively repeated several times. Table 4 includes the results obtained from the fluid bed reactor using 10:1 and 100:1 Cu/Zn weight ratios:

TABLE 4

| Cu/Zn ratio | Phosphorus (ppm) | % Di |
|---|---|---|
| 10:1 | 0 | 87 |
| 10:1 | 500 | 90 |
| 100:1 | 0 | 83.2 |
| 100:1 | 500 | 92.9 |

The above results are average values obtained from several repeat runs which were made to determine whether a statistically significant change occurs with respect to percent dimethyldichlorosilane in methylchlorosilane crude, based on employing phosphorus at different Cu/Zn ratios. No significant statistical increase was found when comparing the 87% Di yield (standard deviation=2) using a Cu/Zn ratio of 10:1 without phosphorus, to the 90% Di yield (standard deviation=3.7) with phosphorus. For instance, upon examination of the standard deviation of the percent dimethyldichlorosilane with and without the phosphorus, the ranges for percent dimethyldichlorosilane overlap. Thus, this was not a statistical increase in the amount of dimethyldichlorosilane produced when there was a high amount of zinc present (Cu/Zn ratio 10:1). However, at a Cu/Zn ratio of 100/1, a statistical increase occurred when the value 83.2% (standard deviation=2.3) was obtained without phosphorus, as compared to the 92.9% (standard deviation= 2.9) obtained with phosphorus.

While typical embodiments have been set forth for the purpose of illustration, the foregoing descriptions should not be deemed to be a limitation on the scope of the invention. Accordingly, various modifications, adaptations, and alternatives may occur to one skilled in the art without departing from the spirit and scope of the present invention.

What is claimed is:

1. A method for promoting the formation of dialkyldihalosilane during direct method alkylhalosilane production, the method comprising effecting reaction between alkyl halide and powdered silicon in the presence of a direct method catalyst comprising copper, silicon, zinc, and phosphorus, where there is maintained during alkylhalosilane formation a reaction mixture comprising, by weight, an average proportion of copper in a range between about 1% and about 5% based on the weight of silicon;

a sufficient amount of zinc to provide a Cu/Zn weight ratio having a value in a range between about 25 and about 250;

and a proportion of phosphorus in a range between about 100 ppm and about 1000 ppm based on the weight of reaction mixture.

2. A method in accordance with claim 1, where the direct method catalyst further comprises tin.

3. A method in accordance with claim 1, where the reaction is conducted in a continuous manner.

4. A method in accordance with claim 1, where the reaction is conducted in a fluid bed reactor.

5. A method in accordance with claim 1, where the reaction is conducted in a fixed bed reactor.

6. A method in accordance with claim 1, where the reaction is conducted in a stirred bed reactor.

7. A method in accordance with claim 1, where the Cu/Zn weight ratio has a value in a range between about 30 and about 200.

8. A method in accordance with claim 1, where the Cu/Zn weight ratio has a value in a range between about 35 and about 100.

9. A method in accordance with claim 1, where the dialkyldihalosilane is dimethyldichlorosilane.

10. A method in accordance with claim 1, where the phosphorus is introduced into the reactor as copper phosphide.

11. A method in accordance with claim 1, where the phosphorus is introduced into the reactor as an alkylphosphine.

12. A method in accordance with claim 11, where the phosphorus is introduced into the reactor as triethylphosphine.

13. A method in accordance with claim 11, where the phosphorus is introduced into the reactor as trimethylphosphine.

14. A method in accordance with claim 1, where the phosphorus is introduced into the reactor as phosphorus trichloride.

15. A method for promoting the formation of dimethyldichlorosilane in a continuous manner during direct method methylchlorosilane production, the method comprising effecting reaction in a fluid bed reactor between methyl chloride and powdered silicon in the presence of a catalyst comprising copper, silicon, zinc, tin, and phosphorus, where there is maintained during methylchlorosilane formation a reaction mixture having an average proportion of copper in a range between about 1% and about 5% based on the weight of silicon;

a sufficient amount of zinc to provide a Cu/Zn ratio having a value in a range between about 30 and about 200;

and a proportion of phosphorus in a range between about 100 ppm and about 1000 ppm, based on the weight of reaction mixture.

16. A method in accordance with claim 15, where the phosphorus is introduced as copper phosphide.

17. A method in accordance with claim 15, where the phosphorus is introduced as phosphorus trichloride.

18. A method in accordance with claim 15, where the phosphorus is introduced as triethylphosphine.

* * * * *